United States Patent [19]

County

[11] 4,134,858

[45] Jan. 16, 1979

[54] CATALYSTS, THEIR MANUFACTURE FOR USE IN DEHYDROGENATION REACTIONS

[75] Inventor: Philippe County, Houilles, France

[73] Assignee: Institut Francais du Petrole, Rueil-Malmaison, France

[21] Appl. No.: 863,002

[22] Filed: Dec. 21, 1977

Related U.S. Application Data

[63] Continuation-in-part of Ser. No. 573,880, May 2, 1975, abandoned.

[30] Foreign Application Priority Data

May 7, 1974 [FR] France .................................. 74 15977

[51] Int. Cl.$^2$ ......................... B01J 29/06; B01J 29/00; B01J 29/10
[52] U.S. Cl. ............................... 252/455 R; 252/454; 252/456; 252/457; 252/458; 252/459; 260/669 R
[58] Field of Search .................... 252/454, 455 R, 458, 252/459; 260/669 R, 683.3

[56] References Cited

U.S. PATENT DOCUMENTS

| 3,100,234 | 8/1963 | Lee .................................. 260/669 R |
| 3,703,593 | 11/1972 | Turley et al. .................... 260/669 R |
| 3,752,773 | 8/1973 | Duke, Jr. et al. ..................... 252/454 |
| 3,867,305 | 2/1975 | Flanigen et al. ................. 260/669 R |

*Primary Examiner*—Carl Dees
*Attorney, Agent, or Firm*—Millen & White

[57] ABSTRACT

Catalyst for dehydrogenating hydrocarbons, as manufactured by the process comprising:

admixing one or more iron compounds, chromium compounds and potassium compounds, in a definite range of relative proportions, moistening and malaxing the resulting mixture while adding thereto a clayish material in such an amount as to obtain by reaction with the potassium compound, a proportion of 3 to 55% b.w. of potassium aluminosilicate in the final catalyst, shaping the homogeneized resulting paste, drying and roasting it at about 870 – 1050° C, the potassium compound being used in an amount greater than that liable to combine with the clayish material.

15 Claims, No Drawings

CATALYSTS, THEIR MANUFACTURE FOR USE IN DEHYDROGENATION REACTIONS

This application is a continuation-in-part of my previous application Ser. No. 573,880, filed May 2, 1975 and now abandoned This invention concerns new catalysts for use in dehydrogenation reactions and, particularly, in reactions for dehydrogenating aliphatic hydrocarbons of low molecular weight (containing for example from 2 to 8 carbon atoms) as well as for dehydrogenating alkylaromatic hydrocarbons (such as ethyl benzene or diethylbenzene), to vinylaromatic hydrocarbons (such as styrene or divinylbenzene). It also concerns a process for the manufacture of these new catalysts. Finally, it also relates to the dehydrogenation process making use of these catalysts.

It is known that dehydrogenation of the above-mentioned hydrocarbons is generally conducted by passing the hydrocarbon, with a high proportion of added steam (2 to 30 moles $H_2O$ per mole of hydrocarbon) over a catalyst, at an hourly rate of liquid hydrocarbon of from 0.1 to 1 volume (at standard temperature and pressure) per volume of catalyst and per hour and at a temperature from about 500 to 700° C.

Among the catalysts described in the prior art for these reactions, one of them, known under the trade mark "Shell 105", has approximately the following composition by weight: $Fe_2O_3$: 83.0%; $K_2O$; 9.0%; $CrO_3$: 3%; $Al_2O_3$: 3%; miscellaneous ($Na_2O$, $SO_3$, $TiO_2$, $SiO_2$, $Mn_3O_4$): 2%. Its filling density in an industrial reactor is from 1.15 to 1.20 metric $T/m^3$, its average mechanical strength, measured on an ERWEKA machine, is 2.35 kg/mm for extrudates of 5 mm diameter and 3-20 mm length, or 1.9 kg/mm for extrudates of 4 mm diameter.

It is obviously interesting to decrease the filling density of such a catalyst. This result can be achieved by means of various porosity-inducing agents, introduced during the manufacture of the catalyst and which disappear during the roasting step. The decrease of the filling density is due in such a case to an increase of the catalyst porosity; of course, it is advantageous, irrespective of the saving of material so achieved, to increase the catalyst porosity, since a higher porosity is generally responsible for a better activity and a higher seleicitivity in the dehydrogenation reaction in which the catalyst is used. However, this result is generally accompanied with a decrease in the mechanical strength of the catalyst.

Turley et al (U.S. Pat. No. 3,703,593) prepare an improved catalyst comprising iron oxide, an alkali metal oxide and a chromium compound, the improvement being achieved by employing both yellow and red iron oxides in particular proportions with respect to each other. Specific binders are silica, alumina cement or portland cement.

The binder is used in low proportion, for example 2.6 to 3.0% or even 3.3% b.w.

Calcination temperatures of 700°–1,000° C are suggested and 700° C is specifically employed.

Lee (U.S. Pat. No. 3,100,234) specifically discloses a catalyst comprising iron oxide, chromium oxide and potassium oxide, the binder being calcium silicate, although other binders are suggested such as silicates, cement, kaolin and the like. The exemplified temperature is 600°–700° C.

Duke et al (U.S. Pat. No. 3,752,773) disclose a method for preparing degradation and attrition-resistant catalyst, which method comprises blending clay with one or more precursor compounds selected from a large group of compounds. Examples of this patent relate to copper chromite catalysts used in the halogen-promoted oxydehydrogenation of hydrocarbons, a reaction quite different from the steam-dehydrogenation of the present invention.

None of the previous workers has appreciated the advantage on yield and selectivity of the steam-dehydrogenation reaction of having a catalyst comprising chromium oxide, iron oxide, 5–40% of potassium alumino-silicate as kaliophyllite and excess potassium oxide, i.e. potassium uncombined with alumina and silica as said potassium alumino-silicate. Nor have they appreciated that such catalyst could only be obtained at calcination temperatures above 850° C, preferably at 870°–1050° C.

It is an object of this invention to describe the manufacture of such a catalyst which gives increased yield and selectivity as compared to the catalysts comprising chromium, iron and potassium compounds, which have not been calcined at 870°–1050° C and which have not a critical content of 5 to 40% b.w. of kaliophyllite of the formula $Al_2O_3$, 2 $SiO_2$, $K_2O$ and an excess of potassium oxide with respect to the potassium oxide engaged in said kaliophyllite.

It has now been discovered that it is possible to obtain catalysts which are simultaneously more active and more selective than those of the prior art and, particularly, than the catalyst "Shell 105", and which, in addition, have simultaneously, at least so good mechanical strength and lower filling density. These catalysts are obtained by associating to iron, chromium and potassium oxides, a determined proportion of at least one potassium alumino-silicate.

As a general rule, the catalysts of the invention are described by their manufacture according to the following succession of steps:

a first step of admixing at least one iron compound, at least one chromium compound and at least one potassium compound, in proportions as hereinafter defined;

a second step of moistening and malaxing the obtained mixture and adding thereto at least one clayish material, in a proportion which will also be defined hereinafter, followed with a homogeneization of the mixture; and a final step of shaping the resulting paste, drying and roasting it at a temperature higher than 850° C and preferably from 870° to 1050° C.

The clayish material is preferably kaolinite or a material providing kaolinite. It is used in such proportion as to provide sufficient $Al_2O_3$ and $SiO_2$ to theoretically permit the formation of kaliophyllite of the formula $Al_2O_3$, 2 $SiO_2$, $K_2O$ in an amount of 5–40% b.w. of the final catalyst; said kaliophyllite forms by reaction of the clayish material, preferably kaolinite, with a portion of the potassium compound at a critical temperature in the range of about 870°–1050° C.

The iron, chromium and potassium compounds are used in proportions corresponding as oxides to ratios by weight:

$$\frac{Fe_2O_3}{K_2O} \text{ from } 1:1 \text{ to } 10:1$$

-continued $$\frac{CrO_3}{K_2O} \text{ from } 0.05:1 \text{ to } 0.4:1, \text{ and}$$

$$\frac{Fe_2O_3}{CrO_3} \text{ from } 15:1 \text{ to } 40:1$$

It is essential that the potassium compound be used in excess with respect to the amount liable to combine with said kaolinite to form said kaliophyllite, thereby forming a final catalyst comprising iron oxide, chromium oxide, 5–40% b.w. kaliophyllite and excess potassium oxide with respect to said kaliophyllite, the respective amounts of iron oxide, chromium oxide and total potassium oxide being in the above proportions.

The above K excess is preferably defined as follows, with respect to the iron and chromium compounds, calculated as oxides:

$$\frac{Fe_2O_3}{K_2O \text{ excess}} \text{ from } 7:1 \text{ to } 10:1$$

$$\frac{CrO_3}{K_2O \text{ excess}} \text{ from } 0.2:1 \text{ to } 0.4:1$$

The iron compound is usually ferric iron oxide, finely crushed (for example to grains of a size smaller than 200 mesh). This iron oxide is advantageously subjected to a preliminary roasting at 800° C. By way of example, there can be used the product manufactured by Société Française d'Electrométallurgie (SOFREM) under the trade mark "HA 160". However, it is possible to replace a portion, e.g. from 5 to 20% by weight, of the total iron oxide by iron hydroxide, obtained by precipitation from an aqueous solution of an iron salt. It is also possible to replace a portion, e.g. from 5 to 20% by weight of the total iron oxide by a thermally decomposable iron salt, such as an iron sulfate, carbonate, acetate, oxalate, citrate, nitrate or alum. It is then possible to make use of ferrous iron salts or ferric iron salts. The chromium compounds, used alone or as mixtures, are usually chromic anhydride, chromic salts, e.g. sodium, potassium or ammonium chromate or bichromate, chromium(III) compounds, e.g. nitrate, sulfate, oxide or hydroxide.

The compounds used for introducing potassium into the catalyst are usually carbonate, oxide and hydroxide. It is also possible to introduce a portion of the potassium, e.g. 1 to 10% by mole, in the form of other salts such for example as sulfate, phosphate or nitrate.

It must be mentioned that, in the manufacture of the catalysts of the invention, it is possible to replace up to 50% by mole of the potassium compound by an equivalent amount of at least one compound of another alkali metal and/or at least one alkaline earth metal compound. In most cases, sodium, calcium or barium compounds are used. In the following, potassium and the metals which may optionally replace it will be referred to in some cases as M.

As clayish materials, it is possible to make use of natural or synthetic products; the term "clayish material" as used for the purpose of describing the present invention, is considered as having its broadest meaning. A clayish material may be defined, as a matter of fact, as an earthy or stony mineral aggregate consisting essentially of hydrous aluminum silicates, plastic when sufficiently pulverized and wetted, rigid when dry, and vitreous when fired at sufficient high temperatures", or alternatively as "a mixture of hydrous silicates of aluminum, iron and magnesium, with or without other rock and mineral particles, said clays being characterized by extreme fineness of particles (often colloidal in size) and by wide variations in physical and thermal (ceramic) properties and in mineral and chemical composition.

Other definitions of the term "clayish material" may be found in the following documents:

THORPES DICTIONARY OF APPLIED CHEMISTRY, vol III, 4th ed. Longmans Green and Co. N.Y. 1953.

ENCYCLOPEDIA OF CHEMICAL TECHNOLOGY KIRK-OTHMER, vol. 6, 2nd ed. Interscience Publishers N.Y. 1965.

By way of example, there will be mentioned clays, kaolinite, halloisite, bentonite, attapulgite and montmorillonite. It is also possible to make use of talc, in admixture with the above-mentioned clayish materials.

The clayish materials are advantageously purified by washing and finely crushed (e.g. to grains smaller than 0.1 mm). Moreover, it is preferred that their halogen content be lower than 5000 ppm.

The thermal activation, conducted at a temperature from 870 to 1050° C, results in a reaction in a solid state between the clayish material and the compounds of metals M, so that an alumino-silicate of metal M is formed.

The alumino-silicate formed with potassium generally consists of kaliophyllite having the molecular composition: $Al_2O_3, 2\ SiO_2, K_2O$. When metal M comprises sodium, the formed alumino-silicate comprises nepheline of molecular composition: $Al_2O_3, 2\ SiO_2, Na_2O$.

The proportion of clayish material which is used for the preparation of the catalyst according to this invention, is such that the catalyst after activation, has a content of kaliophyllite of about 5–40% by weight. The iron, chromium and potassium compounds are used in proportions which correspond, as oxides, to the following ratios by weight:

$$\frac{Fe_2O_3}{K_2O} = \text{from } 1/1 \text{ to } 10/1, \text{ and preferably from } 2/1 \text{ to } 7/1;$$

$$\frac{CrO_3}{K_2O} = \text{from } 0.05/1 \text{ to } 0.4/1, \text{ and preferably from } 0.1/1 \text{ to } 0.3/1, \text{ and}$$

$$\frac{Fe_2O_3}{CrO_3} = \text{from } 15/1 \text{ to } 40/1, \text{ preferably from } 25/1 \text{ to } 35/1.$$

Finally, the proportion of compounds of metals M which is used, calculated as oxides $M_2O$ or $MO$, must be adjusted in accordance with the amount of clayish material used for the preparation of the catalyst.

It is considered, in the case where the oxide $M_2O$ is potassium oxide, that the weight $P_1$ of potassium oxide combined with the clayish material, may be approximately calculated according to the relationship: $P_1 = P_2 \cdot (0.42 \pm 0.03)$, in which $P_2$ is the weight of clayish material involved, expressed as weight of anhydrous material.

When metal M is other than potassium, the formula must be corrected to take into account the molar weight of the oxide $M_2O$ or $MO$. The weight $P'_1$ of metal M oxide, which has the molecular weight $\mu$, is obtained by the relationship:

$$P'_1 = P_2 X \frac{\mu}{94.2} (0.42 \pm 0.03),$$

94.2 being the molar weight of the oxide $K_2O$.

Metals M and particularly potassium, when combined with the clayish material, having a poor catalytic activity, it is necessary to use an amount of potassium compound and, optionally, of another metal M, higher than the amount which is liable to combine with said material.

The amount of the excess of potassium compound to be used is preferably, with the iron compound and the chromium compound, calculated as oxides, such that the ratios by weight $\frac{Fe_2O_3}{K_2O\ exc.}$ is from 7/1 to 10/1 and $\frac{CrO_3}{K_2O\ exc.}$ from 0.2/1 to 0.4/1.

The catalysts of the invention may contain, in addition, from 0.1 to 5% by weight of at least one oxide of at least one metal M' selected from copper, vanadium, zinc, magnesium, manganese, nickel, cobalt, bismuth, tin and antimony. These oxides, acting as dopes, activators, textural promoters, structural promoters or co-catalysts, are added in the form of oxides, hydroxides or thermally decomposable salts, during the manufacture of the catalyst.

It is important that the reactants selected for the manufacture of the catalyst and particularly the reactants introducing potassium and other metals M, contain the smallest possible amount of halogen and particularly of chlorine. Thus it is suitable that the halogen content of the thermally activated catalyst be lower than 1000 ppm and preferably lower than 400 ppm.

Practically, when manufacturing the catalyst of the invention, the homogeneization of the mixture of the starting components may be conducted in a HOBBART malaxator, the resulting paste can be shaped in the form of extrudates, for example by extrusion through an extruding machine ANDOUART, HÜTTE, ALEXANDER WERKE, O'TOOLE or WERNER PLEIDERER. The extrudates may consist, for example, of cylinders whose diameter and height are from 1 to 7 mm. Drying is generally conducted in an oven and the thermal activation in an electric furnace or in a gas furnace.

The catalysts of the invention, when obtained as extrudates of 3 to 6 mm diameter, have generally a filling density, in an industrial reactor from 0.80 to 1.15metric ton/m$^3$, a crushing strength, measured on an Erweka machine, from 1.6 to 3 kg/mm, a porosity, measured by mercury porosimetry, from 18 to 60 ml per 100 g and an average pore diameter from 3000 to 11000 Å.

The following examples illustrate the invention non limitatively. Catalysts A and F are not part of the invention. Catalytic tests of examples 1, 2 and 7 are given by way of comparison.

PREPARATION AND PHYSICAL MEASUREMENTS CARRIED OUT ON THE CATALYSTS

Table I summarizes the conditions of preparation of catalysts A to L and give their structural properties and their centesimal composition. The different proportions mentioned for various salts or hydroxides are expressed as weight of the calcinated oxides ($Fe_2O_3$, $CrO_3$, $K_2O$ . . ).

The preparation of catalysts E and I, is described hereinafter by way of example.

CATALYST E: A press-malaxator O'TOOLE of ARCA OO type, is fed with 2700 g of ferric iron oxide "HA 160" (sold by SOFREM Corporation), 217 g of siderite ($FeCO_3$) and 319 g of ferrous sulfate monohydrate; 147 g of potassium bichromate in aqueous solution (300 ml) and 2940 g of a commercial lye at 50% by weight of potassium hydroxide, containing less than 500 ppm of chlorine, is introduced thereinto while mixing. After homogeneization is achieved by mixing (20 mn), 2400 g of washed kaolinite (Armor Kaoline) is added (said kaolinite presents a loss on ignition at 850° C of 10%).

The mixing step is protracted over 10 minutes and the paste is then extruded to cylinders of 4 mm diameter, which are cut, at the output of the drawing plate to segments having a length of about 2 to 7 mm. After ageing in air for 2 hours, and drying in a ventilated stove for 2 hours at 50° C and 10 hours at 100° C, the extrudates are placed on stainless steel plates NSMC and roasted in a gas furnace at 950° C for 2 hours. The roasting step includes a period of temperature increase (3 to 10 hours) and a cooling period (10 to 30 hours).

CATALYST I: In a HOBBART malaxator, we introduce: 668 g of ferric iron oxide "HA 170" (sold by SOFREM corporation), 270 g of colloidal ferrous hydroxide slurry containing 27.7% by weight of ferric oxide $Fe_2O_3$, consisting essentially of hydrated geothite, 24.8 g of chromic anhydride, 122 g of anhydrous potassium carbonate, 17.6 g of anhydrous potassium sulfate, 21.6 g of bentonite "Bentone 34" (sold by CECA), (loss on ignition = 6% at 850° C)

52.6 g of kaolinite (sold by Prolabo)

57.9 g of barium carbonate.

The mixture is heated to 80° C and 100 ml of water is added thereto so as to obtain a thick paste which is mixed for 45 minutes and then shaped to extrudates of a 5 mm diameter and 2-6 mm length by a piston extruding machine.

The drying and activation conditions are reported in Table I.

The roasting temperature of the catalysts is within the range of from 890° to 1030° C.

The following observations have been made on catalysts prepared according to the invention and particularly, on catalyst B prepared as indicated in table I:

Calcination at about 1000° C of a raw catalyst (or a catalyst preliminarily roasted at a temperature lower than about 850° C) results, as compared to the texture of the same catalyst roasted at about 800° C, in a substantial macroporosity in the range from about 3000 to 11000 Å, and in a porosity increase of about 30–100% without any loss of mechanical strength. Macroscopically, this phenomenon results in an increase of about 5 to 10% of the diameter of the catalyst grains. Table II shows the variations of the textural properties of catalyst B in accordance with the roasting temperature. (Catalysts $B_2$, B and $B_2$).

Catalysts A to L, including $B_1$ and $B_2$, as well as "SHELL 105", have been subjected to long duration catalytic test, conducted in the following conditions:

The catalytic test is carried out in a "catatest" operated under atmospheric pressure and fed with ethylbenzene of industrial grade and with water. The volume of tested catalyst is 100 ml (60 to 120 g). The "Shell 105" catalyst (extrudates of 5 mm diameter, and 3 to 20 mm length) is crushed to fragments of sizes from 3 to 4 mm before the test. Catalysts A to L are shaped as extrudates of 3-6 mm diameter and tested in cylinders of 4-5 mm length and 2-6 mm diameter depending on sintering.

The catalyst is first preheated up to about 500° C. Steam is then introduced and, at about 550° C, ethylbenzene is introduced. The temperature is then regulated so as to obtain a temperature of 614 ± 2° C in the catalyst bed.

The hourly flow rates are as follows:

$$\frac{\text{ethyl benzene}}{\text{catalyst}} = 0.4 \text{ volume } v^{-1}h^{-1} \quad \frac{H_2O}{\text{ethyl benzene}} = 2 \text{ g g}^{-1}$$

Table III below indicates the conversion rate of ethylbenzene, $C_{EB}$, the selectivity to styrene $S_{ST}$, the styrene yield $R_{ST}$, the yields of benzene $R_{BZ}$ and toluene $R_{TOL}$; these different values being expressed as a molar percentage and corresponding to the following definitions:

$$C_{EB} = \frac{\text{moles of converted ethylbenzene}}{\text{moles of introduced ethylbenzene}} \times 100$$

$$S_{ST} = \frac{\text{moles of ethylbenzene converted to styrene}}{\text{moles of converted ethylbenzene}} \times 100$$

$$R_{ST} = \frac{\text{moles of produced styrene}}{\text{moles of introduced ethylbenzene}} \times 100$$

$$R_{BZ} = \frac{\text{moles of produced benzene}}{\text{moles of introduced ethylbenzene}} \times 100$$

$$R_{TOL} = \frac{\text{moles of produced toluene}}{\text{moles of introduced ethylbenzene}} \times 100$$

These various coefficients are interrelated by the following relationships:

$$R_{ST} = C_{EB} \times S_{ST} \times \frac{1}{100} \; ; \; C_{EB} \neq R_{ST} + R_{BZ} + R_{TOL}$$

Examples 1 to 15 thus correspond to the results of the tests conducted in the preceding conditions with "SHELL 105" and catalysts A to L.

From Table III, it is seen that the catalytic performance characteristics of Catalyst A, which contain no alumino-silicate (Example 2), are substantially the same as those of "SHELL 105" (Example 1). Further, the conversion rates and yields in styrene obtained with said catalysts are lower than those obtained with catalysts B - E and G - L (examples 3-6 and 8-13).

Example 7 (catalyst F) shows that a catalyst which does not contain metal M in excess with respect to the amount of metal M liable to combine with the clayish material has a very poor activity.

Examples 3, 14 and 15 show that a catalyst roasted at 800° C has a lower selectivity to styrene, and a catalyst roasted at 1100° C has a lower activity than the same catalyst roasted at 1000° C.

TABLE I

| | | Preparation | | | | Conditions | | | Characteristics | | | | | | Composition | | | | |
|---|---|---|---|---|---|---|---|---|---|---|---|---|---|---|---|---|---|---|---|
| | Starting components | | | | | | | | | | | | | | oxide of metal M | | Clay-ish ma- terial and/or talc % by wt. | double sili- cate of metals M % by wt. | Oxide of metal M' % by wt. |
| Cata- lyst | Iron | Chro- mium | Potas- sium | Metal M other than K | Metal M' | Clayish material | Malaxation time extrusion φ | Drying °C/ time | Roast- ing(1) | vp(2) 2000 bars | drt(3) T/ m(3) | EGG(4) kgF/ mm | Fe2O3 % by weight | CrO3 % by weight | Total % by weight | un- combi- ned % by weight | | | |
| A | Fe2O3=90% Fe(OH)2= 10% | CrO3 | K2CO3 | | | | 30 mn φ 4 mm | 100° C 1h. 150° C 1h. | 920° C 1 h. | 22.0 | 1.14 | 1.9 | 86.4 | 2.9 | 10.75 | 10.75 | 0 | 0 | 0 |
| B | Fe2O3=85% Fe(OH)2= 15% | CrO3 | K2CO3 50% KOH 50% | | | kaolinite | 30 mn φ 4 mm | 100° C 2h. 200° C 1h. | 1000° C 2 h. | 31.9 | 0.97 | 2.6 | 77.9 | 2.6 | 12.60 | 9.70 | 7.1 | 10 | 0 |
| C | Fe2O3 | CrO4K2 | KOH | NaOH | | halloisi- te | 20 mn φ 5 mm | " | 1000° C 1 h. | 21.3 | 1.12 | 2.40 | 72.10 | 2.43 | 8.87K2O 3.67Na2O | ~8.87 | 12.95 | 16.61 | 0 |
| D | Fe2O3=99% Iron citra- te=10% | CrO3 95% Cr(NO3)3 5% | K2CO3 | NaOH | | bentonite | 15 mn φ 4 mm | 100° C 4h. 200° C 1h. | 900° C 2 h. | 23.6 | 1.05 | 2.10 | 61.27 | 2.68 | 7.33K2O 6.41Na2O | 7.33 | 22.31 | 28.72 | 0 |
| E | Fe2O3=90% FeCO3=5% FeSO4=5% | Cr2O7K2 | KOH | | | Kaolinite | 30 mn φ4 mm | 50° C 2h. 100° C 10h. | 950° C 1 h. | 27.8 | 1 | 1.90 | 45.9 | 1.53 | 19.60 | ~4.9 | 33 | 47.7 | 0 |
| F | Fe2O3=90% Fe(OH)2= 10% | CrO3 | KOH | | | kaolinite 60% Talc 40% | 25 mn φ 3 mm | 100° C 2h. 200° C 4h. | 1030° C 2 h. | 34.8 | 0.85 | 2.00 | 49.3 | 1.65 | 13.60 | ~0 | 35.5 | 49.15 | 0 |
| G | Fe2O3 | Cr2O7K2 | KOH | CaCO3 | Cu(OH)2 | Attapul- gite red clay | 60 mn φ 4 mm | 100° C 4h. 200° C 8h. | 890° C 3 h. 940° C 2 h. | 27.1 | 1 | 2.40 | 76.43 | 2.55 | 9.52K2O 1.70CaO | ~9.52 | 6.96 | 8.66 | CuO 2.85% |
| H | Fe2O3 85% FePO4 15% | CrO3 90% Cr(NO3)3 10% | KOH | | Mn2O3 | | 55 mn φ 3 mm | " | | 21.9 | 1.15 | 1.85 | 67.21 | 2.30 | 13.49 | 8.26 | 12.06 | 17.29 | Mn2O3 5% |
| I | Fe2O3 90% Fe(OH)3 10% | CrO3 | K2CO3 90% K2SO4 10% | BaCO3 | Bi2O3 | bentonite 30% kaolinite 70% | 45 mn φ 5 mm | " | 1000° C 2 h. | 24.2 | 1.05 | 2.3 | 74.25 | 2.48 | 9.25K2O 4.50BaO | 9.25 | 6.78 | 11.28 | Bi2O3 2.94% |
| J | Fe2O3 γ 80% Fe2O3 α 20% | CrO3 50% K2Cr2O7 50% | K2CO3 | | Mg(OH)2 | kaolinite | 40 mn φ 4 mm | 100° C 2h. 200° C 4h. | 930° C 1 h. | 33.1 | 0.89 | 2.80 | 58.70 | 2.06 | 16.22 | 6.96 | 21.17 | 30.48 | MgO 1.9% |
| K | Fe2O3 | CrO3 | KOH | | Zn(OH)2 | halloisi- te 50% montmoril- lonite 50% | 60 mn φ 4 mm | " | 920° C 1 h. | 22.8 | 1.12 | 2.60 | 70.04 | 2.38 | 14.06 | 8.61 | 12.57 | 18.02 | ZnO 1% |
| L | Fe2O3 85% Fe2(SO4)3 15% | CrO3 | K2CO3 | VO3NH4 | | bentonite 40% kaolinite 60% | 20 mn φ 4 mm | " | 900° C 2 h. | 23.1 | 1.10 | 1.75 | 74 | 3.47 | 11.97 | 9.21 | 6.74 | 9.5 | V2O5 4% |

(1)This concerns the stage at 7° C. The roasting step further comprises a temperature and a cooling period increase. (3-10 hours)
(2)vp = pore volume
(3)drt = filling density
(4)EGG = crushing grain to grain

TABLE II

Influence of the roasting temperature on the textural and mechanical properties (catalysts $B_1$, B and $B_2$)

| Roasting[1] | | | |
|---|---|---|---|
| T° C | 800 | 1000 | 1100 |
| t hours | 2 | 2 | 2 |
| diameter mm | 3.8 | 4.0 | 4.1 |
| Crushing grain to grain kgF | | | |
| average | 12.9 | 14 | 13.9 |
| max. | >15 | >15 | >15 |
| mini. | 11 | 12.2 | 12 |
| kg/mm | 2.4 | 2.6 | 2.55 |
| Filling density T/m³ | 1.13 | 0.97 | 0.90 |
| Grain density g/ml | 2.04 | 1.80 | 1.6 |
| Structural density g/ml | 4.20 | 4.40 | 4.20 |
| Average pore diameter A | 3000 | 8500 | 10200 |
| Cumulated pore volume at pore diameter = 75A ml/100 g | 24 | 31.9 | 36.6 |
| Total pore volume ml/100 g | 25.2 | 32.8 | 38.3 |
| Specific surface area m²g-1 | 3.4 | 1.4 | 1.1 |

[1]Cf Table I [1]

28 g of alumina cement (Ciment Fondu Lafarge, an alumina cement of high $SiO_2$ content) (A) i.e. about 67% b.w. of the final composition were blended with 10 ml of water and 20 g of potassium carbonate (13.6 g of potassium oxide, i.e. about 33% b.w. of the final composition); after drying at 200° C for 2 hours, a first portion was calcined at 700° C for 2 hours, yielding product $A_1$. A second portion was calcined at 950° C for 2 hours, yielding product $A_2$.

the experiment was repeated with 28 g of Clinker cement (B), a so-called alumina-silica cement sold by Société Thionvilloise des Ciments under Reference No CLK 325; the products $B_1$ and $B_2$ were obtained.

the experiment was repeated with 28 g of silica (C); the products $C_1$ and $C_2$ were obtained.

the experiment was repeated with 28 g of portland cement (D) from Société Lafarge, France; the products $D_1$ and $D_2$ were obtained.

the experiment was repeated with 32 g of Kaolinite (28 g of anhydrous material); the products $E_1$ and $E_2$ were obtained.

the experiment was repeated with 28 g of a mechanical mixture of alumina (12.8 g - 45.9%) and silica (15.2 g - 54.1%); the products $F_1$ and $F_2$ were obtained.

X - Ray study of potassium aluminosilicate formation

TABLE III

| Catalyst | Example No. | Roasting of the Catalyst T° C- time (h)[1] | Ethylbenzene conversion | | Styrene Selectivity | | Styrene yield | | Benzene yield | | Toluene yield | |
|---|---|---|---|---|---|---|---|---|---|---|---|---|
| | | | 10 h. | 6000 h. | 10 h. | 6000 h. | 10 h. | 6000 h. | 10 h. | 6000 h. | 10 h. | 6000 h. |
| SHELL 105 | 1 | — | 68.5 | 61.1 | 89.5 | 90.5 | 61.3 | 55.3 | 2.8 | 1.8 | 4.4 | 4 |
| A | 2 | 920 - 1 h. | 69.6 | 63 | 87.8 | 89.7 | 61.1 | 56.5 | 3 | 2 | 5.5 | 4.5 |
| B | 3 | 1000 - 2 h. | 72.7 | 71.5 | 90 | 91.5 | 65.4 | 65.4 | 2.3 | 2.0 | 5 | 4.1 |
| C | 4 | 1000 - 1 h. | 78.1 | 75.0 | 86.5 | 89.5 | 67.6 | 67.1 | 2.6 | 2.2 | 7.9 | 5.7 |
| D | 5 | 900 - 2 h. | 76.6 | 73.9 | 88.2 | 91.3 | 67.5 | 67.0 | 2.2 | 2.0 | 6.8 | 4.9 |
| E | 6 | 950 - 1 h. | 73.9 | 68.9 | 88.3 | 92 | 65.3 | 63.4 | 2.0 | 1.6 | 6.6 | 3.9 |
| F | 7 | 1030 - 2 h. | 22 | 15 | 91.1 | 90 | 20 | 13.5 | 1.4 | 1.2 | 0.55 | 0.30 |
| G | 8 | 890 - 3 h. | 79 | 73 | 84.8 | 88.9 | 67 | 64.9 | 2.5 | 2.4 | 9.5 | 5.7 |
| H | 9 | 940 - 2 h. | 81 | 72 | 80.2 | 86.1 | 65 | 62 | 4 | 3 | 12 | 7 |
| I | 10 | 1000 - 2 h. | 76.0 | 70.2 | 89.5 | 92.5 | 68.0 | 64.9 | 2.6 | 2.1 | 5.4 | 3.2 |
| J | 11 | 930 - 1 h. | 75.1 | 73.4 | 80.8 | 83.9 | 60.7 | 61.6 | 3.8 | 3.2 | 10.6 | 8.6 |
| K | 12 | 920 - 1 h. | 77.9 | 70.7 | 83 | 89.1 | 64.7 | 63 | 3.4 | 3 | 9.8 | 4.7 |
| L | 13 | 900 - 2 h. | 82 | 75 | 79.5 | 86.5 | 65.2 | 64.9 | 4.6 | 2.8 | 12.2 | 7.3 |
| $B_1$ | 14 | 800 - 2 h. | 74 | 71 | 84.5 | 84.9 | 62.5 | 60.3 | 3.6 | 3.4 | 7.9 | 7.3 |
| $B_2$ | 15 | 1100 - 2 h. | 68.9 | 61 | 90.8 | 89 | 62.6 | 54.3 | 2 | 2 | 4.3 | 4.7 |

[1]Cf. Table I note [1]

In order to compre the effect of various binders to that of a mixture of a clayish material and a potassium compound, and to determine the exact effect to the calcination temperature on performances, the following experiments have been conducted.

STUDY OF THE POTASSIUM ALUMINOSILICATE FORMATION

In order to determine if a chemical reaction occurs between various compounds and potassium carbonate, the following experiments have been made:

is conducted as follows:

After calcining at 700 or 950° C for 2 hours in the air, samples were ground and X - Ray analyzed; the diagrams were compared with the Kaliophyllite (potassium alumino-silicate $Al_2O_3$, 2 $SiO_2$, $K_2O$) diagram, described in A.S.T.M. Index to the powder diffraction data file NRS. 9-471 and 12-134. The results are given in Table IV.

TABLE IV

| Trial serie NR. | | % b.w. Composition without $K_2CO_3$ based on anhydrous material | | | POTASSIUM ALUMINO-SILICATE FORMATION | |
|---|---|---|---|---|---|---|
| | | $Al_2O_3$ | $SiO_2$ | others | Calcination 700° C 2 HRS | Calcination 950° C 2 HRS |
| A | alumina + $K_2CO_3$ cement | 39 | 4.5 | 56.5 (mainly $Fe_2O_3$+CaO) | NO | NO |
| B | alumina-silica cement+$K_2CO_3$ | 11.8 | 28.2 | 60 (48 CaO) | NO | NO |
| C | silica+$K_2CO_3$ | — | 100 | — | NO | NO |
| D | portland cement+$K_2CO_3$ | 6 | 21 | 73 (65 CaO) | NO | NO |
| E | Kaolinite + $K_2CO_3$ mechanical mix- | 44.7 | 52.7 | 2.6 | NO | YES |

TABLE IV-continued

| Trial serie NR. | | % b.w. Composition without $K_2CO_3$ based on anhydrous material | | | POTASSIUM ALUMINO-SILICATE FORMATION | |
|---|---|---|---|---|---|---|
| | | $Al_2O_3$ | $SiO_2$ | others | Calcination 700° C 2 HRS | Calcination 950° C 2 HRS |
| F | ture of alumina +silica+$K_2CO_3$ | 45.9 | 54.1 | 0 | NO | NO |

The diagrams failed to show the presence of potassium alumino-silicate except for the Kaolinite-potassium carbonate mixture, when calcined at 950° C for 2 hours.

This result is clearly unobvious since the above compositions all comprised 67% b.w. of binder, i.e. a sufficient amount (except for silica) to theoretically form at least 5% b.w. potassium alumino-silicate in the calcined product, thus an X-ray detectable amount, as explained hereunder on the basis of theoretical consoderations:
The percent b.w. composition of Kaliophyllite is:
  $Al_2O_3$ = 32.24
  $SiO_2$ = 37.99
  $K_2O$ = 29.77
To obtain a minimal content of 5% of Kaliophyllite in a composition, it is necessary to dispose of at least:
  $Al_2O_3$ = 1.61%
  $SiO_2$ = 1.90%
  $K_2O$ = 1.49%
in said composition.

It is obviously impossible to obtain Kaliophyllite with pure silica in the absence of alumina; with the aluminous cement (A), the minimal cement content b.w. of the finished composition should be:

$$\frac{\text{silica required in product}}{\text{silica in A}} = \frac{1.9}{4.5} \times 100 = 42.2 \% \text{ of aluminous cement.}$$

for clinker cement (B), the minimal content is:

$$\frac{\text{alumina required in product}}{\text{alumina in B}} = \frac{1.61}{11.8} \times 100 = 13.6 \% \text{ of clinker cement.}$$

for portland cement (D), the minimal content is:

$$\frac{\text{alumina required in product}}{\text{alumina in D}} = \frac{1.61}{6} \times 100 = 26.8 \% \text{ of portland cement.}$$

for Kaolinite (E)
Kaolinite composition corresponds closely to the amounts of alumina and silica required for kaliophyllite formation:

$$\frac{\text{alumina required in product}}{\text{alumina in E}} = \frac{1.61}{45.9} \times 100 = 3.5\% \text{ of anhydrous kaolinite as a minimum}$$

for the alumina-silica mixture (F) : 3.5%.

The physical composition is practically identical to the kaolinite composition, but the chemical and cristallographic compositions are quite different. Kaolinite is a mixed hydrate of alumina and silica, corresponding to the formula $$Al_2O_3, 2 SiO_2, 2 H_2O.$$

The unique properties of kaolinite, as compared to other binders, may possibly be explained as follows:

The special acceptor properties toward the alkaline oxides of such a material are due to the very high heat of formation of kaolinite

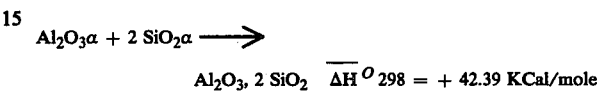

(meta kaolin)

It explains why kaolinite is a very reactive material towards alkaline oxides. Reactivity of physical mixtures of alumina and silica, or of cements containing both alumina and silica is much lower.

It is thus clear that kaolinite and parent clayish materials exhibit unique properties which make them non-equivalent to other binders such as cements or physical mixtures of silica and alumina.

CATALYSTS PREPARTION SERIAL T

The technique of Turley's example 1 was followed with various binders. 2,360 g of hydrated yellow iron oxide, 3,530 g of anhydrous red iron oxide, 1,670 g of potassium carbonate and 250 g of potassium bichromate were mixed with 320 g of kaolinite (280 g of anhydrous material). The mixture was malaxed with a saturated solution of methocel in hot water (60° C), then extruded in pellets having 3/16 inches diameter and length and dried at 200° C for 2 hours.

10 equal samples of the resulting composition were air calcined at the following temperatures and with the following durations

| $T_1$ | 700/1h | $T_6$ | 700/2h |
| $T_2$ | 870/1h | $T_7$ | 870/2h |
| $T_3$ | 900/1h | $T_8$ | 900/2h |
| $T_4$ | 950/1h | $T_9$ | 950/2h |
| $T_5$ | 1100/1h | $T_{10}$ | 1100/2h |

In all cases, the analysis was:

| $Fe_2O_3$ | 77.0 |
| $CrO_3$ | 2.35 |
| $K_2O$ exc. | 15.13 |
| $Al_2O_3$, 2 $SiO_2$, $K_2O$ | 5.52 |

$Al_2O_3$, $SiO_2$ and $K_2O$ are expressed here as $Al_2O_3$, 2 $SiO_2$, $K_2O$ for simplicity of comparison but the above analysis does not mean that kaliophyllite has been effectively formed, which results only from the X - ray diagram inspection.

X - ray diagram of $T_{10}$ product was compared with the X - ray diagram of a mechanical mixture of:
5.5% wt — kaliophyllite
94.5% wt — $T_1$ catalyst (no alumino-silicate formation)
The intensity of the diffraction lines of crystalline kaliophyllite was the same for the two samples, which shows that a 100% reaction had occurred in the $T_{10}$ product, between kaolin and potassium carbonate, as follows:

$$Al_2O_3, 2SiO_2, 2H_2O + K_2CO_3 \xrightarrow[\text{Kaolinite}]{T \geq 870°C}$$

$$\underset{\text{kaliophyllite}}{Al_2O_3, 2SiO_2, K_2O} + CO_2 + 2H_2O$$

The $T_{10}$ product was then taken as standard.

With such a standard, the determination of percentage of kaliohyllite formation with respect to the theoretical 100% formation in the finished catalysts has given the following results:

TABLE V

| Catalysts | % kaliophyllite formed | Catalysts | % kaliophyllite formed |
|---|---|---|---|
| $T_1$ | no formation | $T_6$ | no formation |
| $T_2$ | about 10 | $T_7$ | about 15 |
| $T_3$ | about 80 | $T_8$ | about 90 |
| $T_4$ | 100 | $T_9$ | 100 |
| $T_5$ | 100 | $T_{10}$ | 100 |

It remins relatively unexplained why the above solid state reaction occurs substantilly only at temperatures higher than 850° C. That might be due to the high dilution of clay and potassium oxide in the solid matrix of iron oxide.

The catalysts $T_6$ to $T_{10}$ were tested as explained above.

T = 614° C
$H_2O$/Ethylbenzene = 2g. $g^{-1}$
Ethylbenzene/catlyst/time = 0.4 v. $v^{-1}h^{-1}$
duration of the test = 6 hours.

$$R_{CO + CO_2} \text{ was defined as } \frac{\text{moles of produced CO + CO}_2}{\text{moles of introduced ethylbenzene}}$$

The results after 20 hours testing were

TABLE VI

| Catalyst | Calcination conditions °C Time | C(ethylbenzene conversion) % | S (Styrene selectivity) % | R (Styrene yield) % |
|---|---|---|---|---|
| $T_6$ | 700 / 2 hours | 73.8 | 79.8 | 58.9 |
| $T_7$ | 870 / 2 hours | 73.1 | 84.1 | 61.5 |
| $T_8$ | 900 / 2 hours | 72.9 | 88.0 | 64.1 |
| $T_9$ | 950 / 2 hours | 71.9 | 89.0 | 64.0 |
| $T_{10}$ | 1100/ 2 hours | 65.2 | 92.1 | 60.0 |

The results show the positive effect of a calcination temperature of at least 870° C, but lower than 1100° C, on the yield. Considering the results of the preceeding crystallographic study, the positive effect on activity appears simultaneously with the formation of a potassium alumino-silicate phase which seems responsible of the observed increase of the catalyst activity.

CATALYST PREPARATION SERIAL V

These catalysts had a higher kaliophyllite content, as compared with series T catalysts.

The series T preparation was repeated except that the 320 g of kaolinite were replaced with 2,750 g of kaolinite and 1,501 g of potassium carbonate (the total quantity of potassium carbonate was thus 3,171 g). The malaxing, extruding and drying operations were the same.

5 equal samples of the resulting composition were air calcined as follows:

| | |
|---|---|
| $V_1$ | 700° C 2 hours |
| $V_2$ | 870° C 2 hours |
| $V_3$ | 900° C 2 hours |
| $V_4$ | 950° C 2 hours |
| $V_5$ | 1100° C 2 hours |

The composition of the finished catalyst was:

| | |
|---|---|
| $Fe_2O_3$ | 54.33 |
| $CrO_3$ | 1.66 |
| $K_2O$ (excess) | 10.67 |

$Al_2O_3$, 2 $SiO_2$, $K_2O$ 33.34 (this figure is no indication of kaliophyllite formation as explained above)

The X - ray analysis indicated the following kaliophyllite formation (% of the theoretical yield):

| Catalyst | % kaliophyllite formed |
|---|---|
| $V_1$ | no formation |
| $V_2$ | about 17 |
| $V_3$ | about 92 |
| $V_4$ | 100 |
| $V_5$ | 100 |

The results after 20 hours testing were:

| Catalyst | Calcination temperature (2 hrs at) °C | Ethylbenzene conversion | Styrene selectivity | Styrene yield |
|---|---|---|---|---|
| $V_1$ | 700 | 76.0 | 79.9 | 60.7 |
| $V_2$ | 870 | 75.0 | 84.1 | 63.1 |
| $V_3$ | 900 | 74.8 | 90.2 | 67.5 |
| $V_4$ | 950 | 73.9 | 90.8 | 67.1 |
| $V_5$ | 1100 | 65.2 | 92.3 | 60.2 |

The conclusions are the same as for series T Catalysts although the yields are better (probably due to a higher content of potassium alumino-silicate).

OTHER CATALYST PREPARATIONS (for comparison with series T catalysts)

These preparations conform to the teaching of Turley et al.

The serial T preparation was repeated, with replacement of kaolinite (280 g of anhydrous matinal) with the same weight of the following materials (composition given in Table IV):

| Catalyst | | |
|---|---|---|
| S | alumina cement | |
| R | alumina-silica cement | |
| Q | silica | |
| P | portland cement; this example conforms to example 1 of Turley et al. (USP 3,703,593). | |
| N | physical mixture of alumina and silica (45.9 % – 54.1 %) | |
| M | calcium silicate (as taught by Lee, USP 3,100,234) | |
| L | no binder | |

The catalysts were calcined at 700° C for 2 hours (Serial 1) or at 950° C for 2 hours (Serial 2) and tested as above.

The results were as follows (the results with catalysts $T_6$ and $T_9$ are once more given for comparison)

TABLE VII

| | Kaliophyllite formation | C | S | R |
|---|---|---|---|---|
| $S_1$ | NO | 64.5 | 83.6 | 53.9 |
| $S_2$ | NO | 60.9 | 89.1 | 54.3 |
| $R_1$ | NO | 61.2 | 82.9 | 50.7 |
| $R_2$ | NO | 55.5 | 88.5 | 49.1 |
| $Q_1$ | NO | 67.0 | 83.0 | 55.6 |

TABLE VII-continued

| | Kaliophyllite formation | C | S | R |
|---|---|---|---|---|
| $Q_2$ | NO | 63.9 | 86.9 | 55.5 |
| $P_1$ | NO | 70 | 80.2 | 56.1 |
| $P_2$ | NO | 63.5 | 88.0 | 55.9 |
| $N_1$ | NO | 66.3 | 83.6 | 55.4 |
| $N_2$ | NO | 67.0 | 85.1 | 57.0 |
| $M_1$ | NO | 70.3 | 79.6 | 56.0 |
| $M_2$ | NO | 63.6 | 86.2 | 54.8 |
| $L_1$ | NO | 71.1 | 79.5 | 56.5 |
| $L_2$ | NO | 64.2 | 88.3 | 56.7 |
| $T_6$ | NO | 73.8 | 79.8 | 58.9 |
| $T_9$ | YES (about 5% of catalyst compn.) | 71.9 | 89.0 | 64.0 |

The comparison of Table VI with Table VII shows that:
the portland cement (catalysts $P_1$ and $P_2$) gives catalysts slightly less active than $L_1$ and $L_2$ (without binders).
the others binders, including the physical mixture of alumina and silica, give no positive effect on yield.
Only the clay binders, when associated with potassium oxide and calcined at $T \geqq 870°$ C give a positive effect on the yield.
Considering Table IV, this effect is attributed to the potassium alumino-silicate formation during the calcination step.

I claim:

1. A catalyst comprising iron oxide, chromium oxide, 5-40% by weight of kaliophyllite and excess potassium oxide with respect to said kaliophyllite, especially for dehydrogenating hydrocarbons, as obtained by the process comprising the steps of:
   admixing at least one iron compound, at least one chromium compound and at least one potassium compound;
   moistening and malaxing the resulting mixture and adding thereto at least one clayish material selected from the group consisting of kaolinite, halloisite, bentonite, montmorillonite, attapulgite and mixtures thereof, and homogenizing the mixture to form a paste;
   shaping said paste, drying and roasting it at a temperature of bout 870 – 1050° C, said clayish material being used in such a proportion as to obtain after said roasting a final catalyst containing 5 to 40% by weight of kaliophillite of the formula $Al_2O_3$, 2 $SiO_2$, $K_2O$ as formed by the reaction between said clayish material and a portion of said potassium compound; the iron, chromium and potassium compounds being used in proportions corresponding as oxides, to ratios by weight:

$$\frac{Fe_2O_3}{K_2O} \text{ from 1/1 to 10/1}$$

$$\frac{CrO_3}{K_2O} \text{ from 0.05/1 to 0.4/1, and}$$

$$\frac{Fe_2O_3}{CrO_3} \text{ from 15/1 to 40/1}$$

and said potassium compound being used in excess with respect to the amount liable to combine with said clayish material to form said kaliophyllite, and thereby forming said catalyst.

2. A catalyst according to claim 1, in which said excess of potassium compound is in the following relations to the iron compound and the chromium compound calculated as oxides:

$$\frac{Fe_2O_3}{K_2O \text{ exc.}} \text{ from 7/1 to 10/1, and}$$

$$\frac{CrO_3}{K_2O \text{ exc.}} \text{ from 0.2/1 to 0.4/1}$$

3. A catalyst according to claim 1, in which the iron, chromium or potassium compounds are used in proportions corresponding, as oxides, to ratios by weight:

$$\frac{Fe_2O_3}{K_2O} \text{ from 2/1 to 7/1}$$

$$\frac{CrO_3}{K_2O} \text{ from 0.1/1 to 0.3/1, and}$$

$$\frac{Fe_2O_3}{CrO_3} \text{ from 25/1 to 35/1}$$

4. A catalyst according to claim 1 in which up to 50% by moles of the potassium compound is replaced with an equivalent amount of at least one other alkali-metal compound and/or at least one alkaline-earth metal compound.

5. A catalyst according to claim 4, in which the potassium compound is partially replaced by at least one compound of a metal selected from sodium, calcium and barium.

6. A catalyst according to claim 1, wherein the clayish material is kaolinite.

7. A catalyst according to claim 1, wherein the clayish material is clay.

8. A catalyst according to claim 4, in which up to 50% by moles of the potassium compound is replaced with a sodium compound and the resulting catalyst also comprises nepheline of the molar composition $Al_2O_3$, 2 $SiO_2$, $Na_2O$.

9. A catalyst according to claim 1, further comprising from 0.1 to 5% by weight of at least one oxide of at least one metal selected from copper, vanadium, zinc, magnesium, manganese and bismuth.

10. A catalyst according to claim 9, wherein said oxide is vanadium oxide.

11. A catalyst according to claim 1, in which the roasting step comprises a period of temperature increase of 3 to 10 hours, a stage of 1 to 5 hours at a temperature from 870 to 1050° C, and a cooling period of 10 to 30 hours.

12. A catalyst according to claim 1, having a halogen content lower then 1000 ppm.

13. A catalyst according to claim 1, shaped as extrudates of a 3 to 6 mm diameter, having a filling density in an industrial reactor from 0.80 to 1.15 T/m$^3$, a crushing strength, measured on a Erweka machine, from 1.6 to 3 kg/mm, a porosity, measured by mercury porosimetry, from 18 to 60 ml/100 g and an average pore diameter from 3000 to 11000 Å.

14. A catalyst according to claim 1, wherein the iron compound consists essentially of ferric oxide.

15. A catalyst according to claim 1, wherein the iron compound consists essentially of a mixture of 80 – 95% b.w. of ferric oxide and 5 – 20% b.w. of iron hydroxide, calculated as the corresponding oxide.

* * * * *